United States Patent [19]

Ichinose et al.

[11] 4,259,292
[45] Mar. 31, 1981

[54] GAS DETECTING ELEMENT

[75] Inventors: Noboru Ichinose, Yohohama; Hideo Okuma, Kawasaki; Yuji Yokomizo; Takashi Takahashi, both of Tokyo; Mieko Nishihara, Kawasaki; Masaki Katsura, Mitaka, all of Japan

[73] Assignee: Tokyo Shibaura Electric Co., Ltd., Kawasaki, Japan

[21] Appl. No.: 873,923

[22] Filed: Jan. 31, 1978

[30] Foreign Application Priority Data

Jan. 31, 1977 [JP] Japan .................................. 52-8698

[51] Int. Cl.³ ............................................. G01N 27/12
[52] U.S. Cl. ................. 422/98; 324/715 N; 338/34; 23/232 E
[58] Field of Search .................................. 422/94–98, 422/119; 73/23; 338/34; 23/254 E, 232 E, 255 E; 324/71 SN

[56] References Cited

U.S. PATENT DOCUMENTS

| 3,092,799 | 6/1963 | Baker | 73/254 E UX |
|---|---|---|---|
| 3,507,145 | 4/1970 | Loh | 73/23 |
| 3,631,436 | 12/1971 | Taguchi | 23/254 E X |
| 3,952,567 | 4/1976 | Shinagawa et al. | 23/254 E |
| 3,959,764 | 5/1976 | Allman | 73/254 E X |
| 3,961,248 | 6/1976 | Kawamura | 23/254 E |
| 3,999,947 | 12/1976 | Mihara et al. | 338/34 X |
| 4,015,230 | 3/1977 | Nitta et al. | 73/254 E X |
| 4,036,592 | 7/1977 | Brown et al. | 422/96 X |
| 4,045,177 | 8/1977 | McNally | 23/254 E |
| 4,045,178 | 8/1977 | Okinaka et al. | 23/254 E |
| 4,099,922 | 12/1976 | Yasada | 422/95 |

FOREIGN PATENT DOCUMENTS 51-84291 2/1976 Japan .................................. 422/98

Primary Examiner—Michael S. Marcus
Attorney, Agent, or Firm—Oblon, Fisher, Spivak, McClelland & Maier

[57] ABSTRACT

A gas detecting element comprising a hollow cylindrical insulative body, a pair of electrodes provided on the outer periphery of the insulative body, a gas detecting body covering up the outer periphery of the insulative body and the electrodes, a catalyst layer made of a catalytic material and coated on said gas detecting body, thereby covering up the surface of said gas detecting body, and a heater disposed in the hollow of the insulative body. When the gas detecting element comes into contact with a gas, the surface resistance of the gas detecting body varies, thereby detecting the gas.

9 Claims, 4 Drawing Figures

F I G. 1
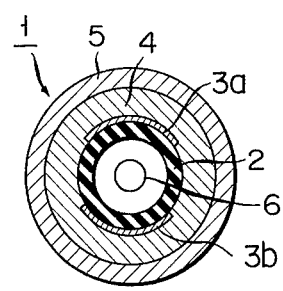
F I G. 2
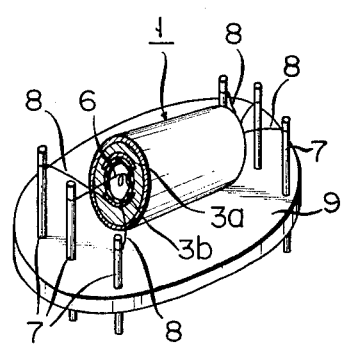

GAS DETECTING ELEMENT

BACKGROUND OF THE INVENTION

This invention relates to a gas detecting element, particularly to a gas detecting element of semiconductor type which detects a gas based on the variation of the surface resistance of a semiconductor body when the semiconductor body is put into contact with the gas.

There are known two types of gas detecting elements. One is the gas detecting element of contact combustion type, and the other is the gas detecting element of semiconductor type.

The gas detecting element of contact combustion type is comprised of a filament, e.g. platinum filament. When the filament comes into contact with a combustible gas, its temperature rises and its electric resistance becomes higher. Based on this resistance elevation the gas detecting element of this type detects the combustible gas. But, the filament evaporates little by little and becomes thinner and thinner since it is heated to a high temperature for a long time. As a result, the electric resistance of the filament becomes higher. Thus the gas detecting element of contact combustion type is defective in view of gas detection accuracy. To eliminate this drawback, some modifications have been proposed. For example, U.S. Pat. No. 3,092,799 shows the technique of embedding a filament in a body made of a heat-resistant oxide such as alumina and silica and impregnating the outer layer portion of the heat-resistant oxide body with an oxidizing catalyst. The gas detecting element thus modified is, however, not a satisfactory one in view of its gas sensitivity and its gas selection characteristic. Further, it does not remain stable during a long use.

The gas detecting element of semiconductor type is comprised of an oxide semiconductor body. When the oxide semiconductor body comes into contact with a gas, its surface resistance varies. Based on this resistance variation the gas detecting element of this type detects the gas. For example, when an N-type semiconductor body made of ZnO, $SnO_2$, $Fe_2O_3$ or the like comes into contact with a reducing gas, its resistance is lowered. Conversely, when the N-type semiconductor body comes into contact with an oxidizing gas, its resistance is elevated. On the other hand, a P-type semiconductor oxide has its resistance elevated when brought into contact with a reducing gas and lowered when put into contact with an oxidizing gas. The gas selection characteristic, i.e. reactivity with various gases, of such a semiconductor oxide is determined by its surface temperature, surface electron level, porosity and pore size etc. Generally, however, such a semiconductor oxide body alone cannot make a satisfactory gas detecting element since its gas sensitivity and gas selection characteristics are insufficient.

Attempts have been made to elevate the gas sensitivity of an oxide semiconductor body. To achieve this object, it was proposed to impregnate an oxide semiconductor body with a catalyst. But this technique proved defective. Namely, the optimum calcination temperature of an oxide semiconductor and that of a catalyst differ so much that it is extremely difficult to determine the temperature at which to calcine the oxide semiconductor and catalyst together, without diminishing their desirable characteristics. Further, the catalyst is likely to exist as a solid solution in the oxide semiconductor body when it is calcinated together with oxide at a high temperature or while the resultant gas detecting element is used at a high temperature (To elevate its gas sensitivity, the element is preferably heated by a heater to maintain its surface temperature at a few hundred degrees centigrade.). As the catalyst is reformed into a solid solution in the oxide semiconductor body the gas sensitivity of the element is reduced and the aging of the element promoted.

SUMMARY OF THE INVENTION

An object of this invention is to provide a gas detecting element of semiconductor type which has a high gas sensitivity and a good gas selection characteristic, which is slow in aging and which can be easily manufactured.

The gas detecting element according to this invention comprises a hollow cylindrical insulative body, a pair of electrodes provided on the outer periphery of the insulative body, a gas detecting body made of ZnO-based semiconductor and covering up the outer periphery of the insulative body and the electrodes, and a catalyst layer made of a catalytic material and coated on the gas detecting body, thereby covering up the surface of the gas detecting body.

BRIEF DESCRIPTION OF THE DRAWINGS

FIG. 1 is a cross-sectional view of a gas detecting element according to this invention;

FIG. 2 is a perspective view of a device using the gas detecting element shown in FIG. 1;

DETAILED DESCRIPTION OF THE PREFERRED EMBODIMENTS

Figure 3:
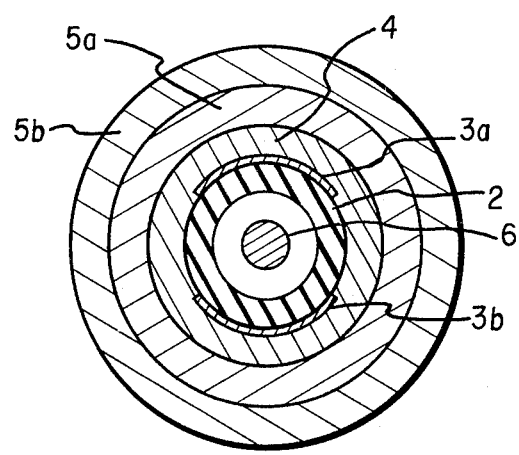
FIG. 3 is a cross-sectional view of a gas detecting element having two catalyst layers within the scope of the present invention.

As shown in FIG. 1, a gas detecting element 1 according to this invention is a hollow cylinder. It comprises a hollow cylindrical insulative body 2, a pair of electrodes 3a and 3b provided on the outer periphery of the insulative body 2, and a gas detecting body 4 made of a ZnO-based semiconductive material and covering up the insulative body 2 and the electrodes 3a and 3b. Further, a catalyst layer 5 about 10 to 100 microns thick is coated on the outer periphery of the gas detecting body 4. In the hollow of the insulative body 2 there is disposed a heater 6.

The hollow cylindrical insulative body 2 may be made of any electrically insulative material that remains heat-resistant at the temperature at which the gas detecting element 1 is used. For example, it may be made of ceramics such as $SiO_2$—$Al_2O_3$ and $Al_2O_3$. The gas detecting body may be made of any oxide semiconductor comprising ZnO. For example, the gas detecting body is made of ZnO—$Me_2O$—$Me'_2O_3$ (Me=Li, Na, K or Rb; Me'=Ga, B, In, Fe, Al or Cr), ZnO—MeO—$Me'_2O_3$ (Me=Ca, Sr, Ba, Co, Ni or Mn; Me'=Ga, B, In, Fe, Al or Cr), ZnO—$Me_2O_3$—$Me'_2O_3$ (Me=Sc, Y or La; Me'=Ga, B, In, Fe, Al or Cr), ZnO—$MeO_2$—$Me'_2O_3$ (Me=Ti, Zr, Hf, Sn or Ge; Me'=Ga, B, In, Fe, Al or Cr), ZnO—$Me_2O_5$—$Me'_2O_3$ (Me=Nb, Ta, Sb or V; Me'=Ga, B, In, Fe, Al or Cr) or ZnO—$MeO_3$—$Me'_2O_3$ (Me=Mo, W or Te; Me'=Ga, B, In, Fe, Al or Cr).

The catalyst layer 5 coated on the gas detecting body 4 is made of an oxidizing catalyst such as Pt, Pd, Ag, Cu, Co, Ni and a chloride of any one of these metals. Further, it may be made of $V_2O_5$, $MoO_3$, NiO, $Cr_2O_3$, MgO, $Fe_2O_3$ or the like. Preferably, any one of these oxidizing catalysts should be used, being carried by carriers such a $Al_2O_3$, $SiO_2$, $ZrO_2$, etc. or by carriers made of a composite material of these oxides.

In another embodiment of the invention as shown in FIG. 3, the gas detecting element 1 is provided with a second catalyst layer 5b which covers underlying first catalyst layer 5a which in turns covers underlying gas detecting body 4. The types of catalysts employed in the catalyst layers vary as a function of the types of gases the gas detecting element is designed to detect.

The heater 6 for heating the gas detecting body 4 may be of a coil type or any other type. It is employed to elevate the gas sensitivity of the gas detecting body 4. It may be detachably disposed in the hollow cylindrical insulative body 2, and thus may be taken out from the hollow of the insulative body 2 when it is unnecessary.

The gas detecting element 1 is manufactured, for example, in the following way.

First, $SiO_2$ and $Al_2O_3$, which serve as catalyst carriers, are mixed thoroughly in the mixing ratio of 2:3 by weight. The mixture thus prepared is then presintered at 1,000° to 1,800° C. to form a mullite compound. The mullite compound is ground into a fine powder by a grinder such as a bowl mill or a pot mill. A prescribed amount of the powder is put into a solution, e.g. $H_2PtCl_6 \cdot 6H_2O$. The mullite compound powder and the solution are then stirred by a magnet stirrer or the like, while being dried. The dried mixture of the powder and the solution is grinded in a mortar into powder. This powder is calcined to form a cake. The cake is grinded into a catalyst powder. $SiO_2$—$Al_2O_3$ in the catalyst thus obtained is an acid catalyst and possesses a heat resistance. Thus it functions as both a catalyst and a catalyst carrier.

Thereafter, a ZnO-based oxide semiconductive material is coated on the insulative body 2 provided with the electrodes 3a and 3b and then dried and calcined, thereby forming the gas detecting body 4. This done, the catalyst prepared as mentioned above is dissolved in an appropriate solution to form a slurry. This slurry is coated on the outer surface of the gas detecting body 4, and then is dried and finally calcined at 300° to 1,000° C.

Figure 4:
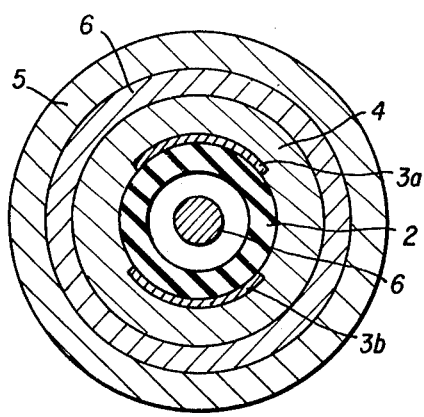
FIG. 4 is a cross-sectional view of a gas detecting element having a partition layer positioned between the underlying ZnO-based semiconductor layer and the overlying catalyst layer.

In another embodiment of the present gas detecting element as shown in FIG. 4, a partition layer 6 can be deposited on the gas detecting body 4 and thereafter catalyst layer 5 is deposited on the partition layer 6 and then dried and calcined as described above. In this structure the catalyst layer 6 is separated from the gas detecting body. A suitable partition layer 6 can be formed from a mixture of mullite in a binder paste.

Of course the catalyst can also be used unassisted by a catalyst carrier. For example, platinum black may be mixed with water or any other appropriate binder to form a catalyst paste. Then, the gas detecting body 4 is calcined at 300° to 1,000° C. This done, the catalyst paste is coated on the gas detecting body 4, thereby forming a catalyst layer 5.

The gas detecting element 1 manufactured as mentioned above may be fabricated on pins 7 as illustrated in FIG. 2. More specifically, the element 1 is connected by means of lead wires 8 to the pins 7 which are planted on an insulative plate 9.

As described above, the gas detecting body made of a ZnO-based oxide semiconductive material is separately formed from a catalyst layer. Thus, the diffusion of the catalyst into the gas detecting body is suppressed over a long use of the gas detecting element, and the gas detecting element is therefore slow in aging. Further, the gas sensitivity of the gas detecting element can be highly improved.

Moreover, if the catalyst layer is a mixture of a carrier such as $Al_2O_3$, $SiO_2$, $ZrO_2$, etc. or a carrier made of a composite material of these oxides and an oxidizing catalyst, in particular, a chloride of Pt, Pd or the like, then the gas sensitivity of the gas detecting element will vary much less over a long use of the gas detecting element. The rate of gas sensitivity variation is small perhaps for the following reason.

First, the catalyst seems to preserve its own catalytic effect for a long time since the catalyst layer 5 is formed separately from the gas detecting body 4 and the catalyst, e.g. $PtCl_2$ does not form a solid solution with the gas detecting body 4. Secondly, unlike the conventionally used Pt, Pd or the like and an oxide thereof, a catalyst made of a mixture of $PtCl_2$ and a silica- or alumina-based compound is relatively free of grain growth and thus free of surface reduction because it is a chloride. In addition, since it is carried by a heat-resistant, silica-based or alumina-based compound, the catalyst seems to maintain its large surface area.

Several gas detecting elements outside the scope of this invention (hereinafter called "reference elements") were manufactured, and several gas detecting elements within the scope of this invention (hereinafter called "embodiments") were made. Their compositions are as listed below:

Reference Element 1 . . . The gas detecting body contains 0.3% by weight of $H_2PtCl_6 \cdot 6H_2O$.

Reference Element 2 . . . The gas detecting body is impregnated with $H_2PtCl_6 \cdot 6H_2O$.

Reference Element 3 . . . The gas detecting body contains 0.3% by weight of platinum black.

Reference Element 4 . . . The gas detecting body contains 5% by weight of $3Al_2O_3$—$2SiO_2$ containing 5% by weight of Pt.

Reference Element 5 . . . A gas detecting element of contact combustion type, using a Pt filament.

Embodiment 1 . . . The gas detecting body is coated with a catalyst layer made of $Al_2O_3$ added with 0.3% by weight of $PtCl_2$.

Embodiment 2 . . . The gas detecting body is coated with a catalyst layer made of $SiO_2$ added with 0.25% by weight of $PtCl_2$.

Embodiment 3 . . . The gas detecting body is coated with a catalyst layer made of $3Al_2O_3$—$SiO_2$ carrying 0.4% by weight of $PtCl_2$.

Embodiment 4 . . . The gas detecting body is coated with a catalyst layer made of $3Al_2O_3$—$2SiO_2$ added with 0.4% by weight of $PtCl_2$.

Embodiment 5 . . . The gas detecting body is coated with a catalyst layer made of $Al_2O_3$—$5SiO_2$ added with 0.4% by weight of $PtCl_2$.

Embodiment 6 . . . The gas detecting body is coated with a catayst layer made of $ZrO_2$ carrying 0.4% by weightof $PtCl_2$.

Embodiment 7 . . . The gas detecting body is coated with a mullite layer, and the mullite layer is then coated with a catalyst layer made of $3Al_2O_3$—$2SiO_2$ added with 0.4% by weight of $PtCl_2$.

Embodiment 8 ... The gas detecting body is coated with a mullite layer, and the mullite layer is then coated with a catalyst layer made of platinum black.

Embodiment 9 ... The gas detecting body is coated with a catalyst layer made of platinum black.

The gas detecting body of any one of the reference elements 1 to 5 and the embodiments 1 to 9 is made $ZnO-Ga_2O_3-Sb_2O_5$.

The characteristics of the reference elements and the embodiments of this invention were measured and are as shown in the following Table 1. In Table 1, "Ro" denotes the electric resistance which each reference element or embodiment showed when put in contact with air, "Rg" the electric resistance which each element or embodiment showed when put in contact with a 0.2%-gas, and "Ro/Rg" the gas sensitivity of each element or embodiment. "Variation of Gas Sensitivity" shows how much the gas sensitivity of each element or embodiment has varied over 1,000 hours.

sensitive to $C_4H_{10}$, as shown in the following Table 2. As shown also in Table 2, this gas detecting element is very good in sensitivity preservation.

TABLE 2

|  | Gas detecting element using Pt-based catalyst | | Gas detecting element using Pd-based catalyst | | Ro or Rg after 1,000 Hrs. |
|---|---|---|---|---|---|
| Ro |  | 1,000KΩ | Ro/Rg | 970KΩ | Ro/Rg | −7% |
| $C_4H_{10}$ | 115KΩ | 8.7 | 900KΩ | 0.9 | −3% |
| Rg $H_2$ | 850KΩ | 1.2 | 96KΩ | 10.0 | +2% |
| CO | 870KΩ | 1.2 | 130KΩ | 7.5 | +2% |

As described above in detail, the gas detecting element according to this invention is good in gas sensitivity, gas selection characteristic and sensitivity preservation. In addition, its gas sensitivity and gas selection characteristic can be adjusted according to its particular use, merely by properly selecting the material of the

TABLE 1

|  | Ro | Rg (Ro/Rg) $C_4H_{10}$ | $H_2$ | CO | Ro after 1,000 Hrs. | Rg to $C_4H_{10}$ after 1,000 Hrs. | Gas sensitivity | Gas selection characteristic | Sensitivity preservation |
|---|---|---|---|---|---|---|---|---|---|
| RE 1 | 1,500KΩ | 300KΩ (5.0) | 1,000KΩ (1.5) | 1,100KΩ (1.4) | −40% | −20% | Good | Good | Bad |
| RE 2 | 3,000KΩ | 700KΩ (4.3) | 2,200KΩ (1.4) | 2,500KΩ (1.2) | +120% | +140% | Good | Good | Bad |
| RE 3 | 400KΩ | 300KΩ (1.3) | 330KΩ (1.2) | 330KΩ (1.2) | −10% | −8% | Bad | Bad | Good |
| RE 4 | 1,100KΩ | 180KΩ (6.1) | 450KΩ (2.4) | 490KΩ (2.2) | −15% | −10% | Good | Good | Bad |
| RE 5 | 3.28Ω | 3.35Ω (0.9) | 3.31Ω (0.9) | 3.30Ω (0.9) | 0% | −1% | Bad | Bad | Good |
| E 1 | 1,226KΩ | 176KΩ (7.0) | 1,117KΩ (1.1) | 1,130KΩ (1.1) | −3% | −2% | Good | Good | Good |
| E 2 | 1,028KΩ | 188KΩ (5.5) | 925KΩ (1.1) | 944KΩ (1.1) | −5% | −3% | Good | Good | Good |
| E 3 | 1,620KΩ | 203KΩ (8.0) | 1,537KΩ (1.1) | 1,495KΩ (1.1) | −1% | −2% | Good | Good | Good |
| E 4 | 800KΩ | 100KΩ (8.0) | 700KΩ (1.1) | 710KΩ (1.1) | −7% | −3% | Good | Good | Good |
| E 5 | 770KΩ | 98KΩ (7.9) | 660KΩ (1.2) | 690KΩ (1.1) | −8% | −2% | Good | Good | Good |
| E 6 | 910KΩ | 150KΩ (6.1) | 830KΩ (1.1) | 850KΩ (1.1) | −5% | −4% | Good | Good | Good |
| E 7 | 350KΩ | 250KΩ (14) | 3,150KΩ (1.11) | 3,300KΩ (1.01) | −2% | −1% | Good | Good | Good |
| E 8 | 1,380KΩ | 180KΩ (7.2) | 380KΩ (3.42) | 470KΩ (2.70) | −3% | −4% | Good | Good | Good |
| E 9 | 430KΩ | 72KΩ (5.97) | 105KΩ (4.1) | 130KΩ (3.3) | −5% | +3% | Good | Fair | Good |

As Table 1 shows, the embodiments 1 to 9, each comprising a gas detecting body made of a ZnO-based oxide semiconductive material and a Pt-based catalyst layer, showed a good sensitivity to to $C_4H_{10}$ (iso-butane gas). They are good in respect of gas sensitivity, gas selection characteristic and sensitivity preservation. On the other hand, each reference element, whose gas detecting body contains a catalyst or is impregnated with a catalyst, did not show a sufficient gas sensitivity, a good gas selection characteristic or a good sensitivity preservation.

The gas detecting element according to this invention can be highly sensitive to a specific one of various gases if the catalyst is selected appropriately. For example, the gas detecting element may comprises a gas detecting body made of $ZnO-Ga_2O_3-Sb_2O_5$ and a catalyst layer made of $3Al_2O_3-2SiO_2$ (carrier) and $PdCl_2$ (catalyst) occupying 0.4% by weight of $3Al_2O_3-2SiO_2$. Unlike a gas detecting element using a Pt-based catalyst, this element is highly sensitive to $H_2$ and CO but not so catalyst layer and the material of the gas detecting body. Further, the calcination temperature for preparing the catalyst layer and the gas detecting body can be easily controlled during the manufacture of the element.

What we claim is:

1. A gas detecting element comprising a hollow cylindrical insulative body, a pair of electrodes provided on the outer periphery of said insulative body, a gas detecting body made of a porous ZnO-based semiconductor and covering up the outer periphery of said insulative body and said electrodes, and a catalyst layer made of a catalytic material and coated on said gas detecting body, thereby covering up the surface of said gas detecting body.

2. The gas detecting element according to claim 1, wherein a heater for heating said gas detecting body is detachably disposed in the hollow of said insulative body.

3. The gas detecting element according to claim 1, wherein said catalyst layer is comprised of a carrier selected from the group consisting of $Al_2O_3$, $SiO_2$, $ZrO_2$ and a composite material of these oxides and an oxidizing catalyst carried by said carrier.

4. The gas detecting element according to claim 1, wherein said catalyst layer is made of a material selected from the group consisting of Pt, Pd, a chloride of Pt and a chloride of Pd.

5. The gas detecting element according to claim 1, wherein said catalyst layer is made of an oxidizing catalyst selected from the group consisting of Ag, Cu, Co, Ni, a chloride of any one of these metals, $V_2O_5$, $MoO_3$, NiO, $Cr_2O_3$, MgO and $Fe_2O_3$.

6. The gas detecting element according to claim 1, wherein said gas detecting body is made of a ZnO-based semiconductor selected from the group consisting of $ZnO-Me_2O-Me'_2O_3$ (Me=Li, Na, K or Rb; Me'=Ga, B, In, Fe, Al or Cr), $ZnO-MeO-Me'_2O_3$ (Me=Ca, Sr, Ba, Co, Ni or Mn; Me'=Ga, B, In, Fe, Al or Cr), $ZnO-Me_2O_3-Me'_2O_3$ (Me=Sc, Y or La; Me'=Ga, B, In, Fe, Al or Cr), $ZnO-MeO_2-Me'_2O_3$ (Me=Ti, Zr, Hf, Sn or Ge; Me'=Ga, B, In, Fe, Al or Cr), $ZnO-Me_2O_5-Me'_2O_3$ (Me=Nb, Ta, Sb or V; Me'=Ga, B, In, Fe, Al or Cr) or $ZnO-MeO_3-Me'_2O_3$ (Me=Mo, W or Te; Me'=Ga, B, In, Fe, Al or Cr).

7. The gas detecting element according to claim 1, wherein a partition layer is formed between said catalyst layer and said gas detecting body, thereby suppressing the diffusion of the catalyst in said catalyst layer into said gas detecting body.

8. The gas detecting element according to claim 7, wherein said partition layer is made of mullite.

9. A gas detecting element, comprising: a hollow cylindrical insulative body; a pair of electrodes provided on the outer periphery of said insulative body; a gas detecting body made of a porous ZnO-based semiconductor which covers the outer periphery of said insulative body and said electrodes; a first catalyst layer consisting of a catalytic material deposited on said gas detecting body such that it covers said gas detecting body; and a second catalyst layer consisting of a different catalytic material deposited on and covering said first catalyst layer.

* * * * *